US010588850B2

(12) United States Patent
Fondin et al.

(10) Patent No.: US 10,588,850 B2
(45) Date of Patent: Mar. 17, 2020

(54) COSMETIC COMPOSITION COMPRISING HYDROPHOBIC SILICA AEROGEL PARTICLES, A WAX, A HYDROCARBON OIL AND A FATTY ALCOHOL AND/OR A FATTY ACID

(71) Applicant: L'OREAL, Paris (FR)

(72) Inventors: Thomas Fondin, Taverny (FR); Virginie Masse, Courbevoie (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/410,265

(22) PCT Filed: Jun. 21, 2013

(86) PCT No.: PCT/EP2013/062964
§ 371 (c)(1),
(2) Date: Dec. 22, 2014

(87) PCT Pub. No.: WO2013/190080
PCT Pub. Date: Dec. 27, 2013

(65) Prior Publication Data
US 2015/0366783 A1  Dec. 24, 2015

Related U.S. Application Data

(60) Provisional application No. 61/695,321, filed on Aug. 31, 2012, provisional application No. 61/695,323, filed on Aug. 31, 2012.

(30) Foreign Application Priority Data

Jun. 21, 2012 (FR) ..................... 12 55820
Jun. 21, 2012 (FR) ..................... 12 55821

(51) Int. Cl.
| | |
|---|---|
| A61K 8/00 | (2006.01) |
| A61K 8/92 | (2006.01) |
| A61K 8/34 | (2006.01) |
| A61K 8/36 | (2006.01) |
| A61K 8/02 | (2006.01) |
| A61K 8/25 | (2006.01) |
| A61K 8/31 | (2006.01) |
| A61Q 5/06 | (2006.01) |

(52) U.S. Cl.
CPC ............ *A61K 8/922* (2013.01); *A61K 8/0279* (2013.01); *A61K 8/25* (2013.01); *A61K 8/31* (2013.01); *A61K 8/342* (2013.01); *A61K 8/361* (2013.01); *A61Q 5/06* (2013.01); *A61K 2800/612* (2013.01); *A61K 2800/651* (2013.01)

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |
| 2,723,248 A | 11/1955 | Wright |
| 3,211,618 A * | 10/1965 | Kambersky ............ A61K 8/06 514/787 |
| 3,579,629 A | 5/1971 | Pasero et al. |
| 3,589,978 A | 6/1971 | Kamal et al. |
| 3,716,633 A | 2/1973 | Viout et al. |
| 3,734,874 A | 5/1973 | Kibler et al. |
| 3,779,993 A | 12/1973 | Kibler et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,119,680 A | 10/1978 | Vachon |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |
| 4,300,580 A | 11/1981 | O'Neill et al. |

(Continued)

FOREIGN PATENT DOCUMENTS

| | | |
|---|---|---|
| DE | 2330956 A1 | 1/1974 |
| DE | 102005052585 A1 | 5/2007 |

(Continued)

OTHER PUBLICATIONS

International Search Report and Written Opinion for PCT/EP2013/062964 dated Jun. 21, 2013).

(Continued)

*Primary Examiner* — Susan T Tran
(74) *Attorney, Agent, or Firm* — The Marbury Law Group, PLLC

(57) ABSTRACT

The present invention relates to a cosmetic composition comprising:
 hydrophobic silica aerogel particles,
 at least one wax,
 at least one hydrocarbon oil and
 at least one fatty alcohol and/or at least one fatty acid, the composition comprising at least 10% by weight of wax(es), with respect to the total weight of the composition.

17 Claims, No Drawings

(56) References Cited

U.S. PATENT DOCUMENTS

| | | | |
|---|---|---|---|
| 4,693,935 A | 9/1987 | Mazurek | |
| 4,728,571 A | 3/1988 | Clemens et al. | |
| 4,972,037 A | 11/1990 | Garbe et al. | |
| 4,973,656 A | 11/1990 | Blount | |
| 5,660,816 A | 8/1997 | Adams et al. | |
| 5,662,893 A | 9/1997 | George et al. | |
| 5,674,479 A | 10/1997 | George et al. | |
| 6,106,813 A | 8/2000 | Mondet et al. | |
| 6,166,093 A | 12/2000 | Mougin et al. | |
| 6,274,152 B1* | 8/2001 | Brieva | A61K 8/25 424/400 |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 7,063,834 B2 | 6/2006 | Mougin et al. | |
| 7,470,725 B2 | 12/2008 | Schwertfeger et al. | |
| 8,021,651 B2 | 9/2011 | Hentrich et al. | |
| 2002/0037256 A1 | 3/2002 | Nocerino et al. | |
| 2002/0150546 A1 | 10/2002 | Mougin et al. | |
| 2003/0191271 A1 | 10/2003 | Mondet et al. | |
| 2004/0180069 A1 | 9/2004 | Bleuez et al. | |
| 2006/0239953 A1* | 10/2006 | Clapp | A61K 8/31 424/70.22 |
| 2008/0233071 A1 | 9/2008 | Hentrich et al. | |
| 2009/0061004 A1* | 3/2009 | Birkel | A61K 8/046 424/489 |
| 2009/0105353 A1* | 4/2009 | Lorant | A61K 8/06 514/772.3 |
| 2010/0209376 A1 | 8/2010 | Richters et al. | |
| 2011/0300092 A1* | 12/2011 | Kambach | A61K 8/8147 424/70.7 |
| 2012/0288546 A1* | 11/2012 | Michos | A61K 8/0279 424/401 |
| 2013/0210694 A1 | 8/2013 | Palla-Venkata et al. | |
| 2013/0287828 A1* | 10/2013 | Cassin | A61K 8/042 424/401 |
| 2013/0337026 A1* | 12/2013 | Cassin et al. | 424/401 |

FOREIGN PATENT DOCUMENTS

| | | |
|---|---|---|
| DE | 102005060435 A1 | 6/2007 |
| DE | 102007052391 A1 | 5/2009 |
| DE | 102007053616 A1 | 5/2009 |
| EP | 0412704 A2 | 2/1991 |
| EP | 0412707 A1 | 2/1991 |
| EP | 0582152 A2 | 2/1994 |
| EP | 0619111 A1 | 10/1994 |
| EP | 0637600 A1 | 2/1995 |
| EP | 0640105 A1 | 3/1995 |
| EP | 0648485 A1 | 4/1995 |
| EP | 0656021 A1 | 6/1995 |
| EP | 0751162 A1 | 1/1997 |
| EP | 1457191 A2 | 9/2004 |
| EP | 2248513 A1 | 11/2010 |
| FR | 1222944 A | 6/1960 |
| FR | 1400366 A | 5/1965 |
| FR | 1564110 A | 4/1969 |
| FR | 1580545 A | 9/1969 |
| FR | 2077143 A | 10/1971 |
| FR | 2265781 A1 | 10/1975 |
| FR | 2265782 A1 | 10/1975 |
| FR | 2350384 A1 | 12/1977 |
| FR | 2357241 A2 | 2/1978 |
| FR | 2393573 A1 | 1/1979 |
| FR | 2439798 A1 | 5/1980 |
| FR | 2743297 A1 | 7/1997 |
| FR | 2814067 A1 | 3/2002 |
| FR | 2814068 A1 | 3/2002 |
| GB | 839805 A | 6/1960 |
| GB | 922457 A | 4/1963 |
| GB | 1021400 A | 3/1966 |
| GB | 1331819 A | 9/1973 |
| GB | 1572626 A | 7/1980 |
| JP | 2011246352 A | 12/2011 |
| LU | 75370 A1 | 2/1978 |
| LU | 75371 A1 | 2/1978 |
| WO | 93/23009 A1 | 11/1993 |
| WO | 93/23446 A2 | 11/1993 |
| WO | 94/03510 A1 | 2/1994 |
| WO | 95/00578 A1 | 1/1995 |
| WO | 95/18191 A1 | 7/1995 |
| WO | 97/08261 A1 | 3/1997 |
| WO | 97/20899 A1 | 6/1997 |
| WO | 01/45651 A1 | 6/2001 |
| WO | 2005/070374 A1 | 8/2005 |
| WO | 2007/051511 A1 | 5/2007 |
| WO | 2009/059869 A2 | 5/2009 |
| WO | 2010/054980 A1 | 5/2010 |
| WO | 2011/148328 A2 | 12/2011 |
| WO | 2013/190077 A2 | 12/2013 |
| WO | 2013/190078 A2 | 12/2013 |

OTHER PUBLICATIONS

English language abstract for DE 102005060435 (Jun. 21, 2007).
English language abstract for DE 102007053616 (May 14, 2009).
English language abstract for JP 2011246352 (Dec. 8, 2011).
International Search Report and Written Opinion of counterpart Application No. PCT/EP2013/062961, dated Dec. 13, 2013.
International Search Report and Written Opinion of counterpart Application No. PCT/EP2013/062960, dated Jul. 16, 2014.
Porter, M.R., "Handbook of Surfactants," published by Blackie & Son (Glasgow and London), 1991, pp. 116-178.
"Silica Silylate Aerogel for Cosmetic Applications," IP.Com Journal, IP.Com Inc., West Henrietta, NY, XP013112635, Jan. 30, 2006.
Dow Coming® VM-2270 Aerogel Fine Particles (Aug. 24, 2012).
Non-Final Office Action for co-pending U.S. Appl. No. 14/410,298, dated Mar. 18, 2016.
Non-Final Office Action for co-pending U.S. Appl. No. 14/410,287, dated May 24, 2016.
Final Office Action for co-pending U.S. Appl. No. 14/410,298, dated Dec. 5, 2016.
Final Office Action for copending U.S. Appl. No. 14/410,298, dated Sep. 26, 2018.
Non-Final Office Action for copending U.S. Appl. No. 14/410,287, dated Nov. 29, 2018.
Final Office Action for copending U.S. Appl. No. 14/410,287, dated Sep. 29, 2017.
Non-Final Office Action for copending U.S. Appl. No. 14/410,298, dated Feb. 12, 2018.
Co-pending U.S. Appl. No. 16/363,476, Cosmetic Composition Comprising Hydrophobic Silica Aerogel Particles and a Fixing Polymer, Inventors: Cécile Bebot et al., filed Mar. 25, 2019.
Non-Final Office Action for co-pending U.S. Appl. No. 14/410,298, dated Apr. 5, 2019.
Final Office Action for co-pending U.S. Appl. No. 14/410,287, dated Jun. 12, 2019.
Final Office Action for co-pending U.S. Appl. No. 14/410,298, dated Sep. 12, 2019.
Final Office Action for co-pending U.S. Appl. No. 14/410,287, dated Nov. 29, 2019.

* cited by examiner

COSMETIC COMPOSITION COMPRISING HYDROPHOBIC SILICA AEROGEL PARTICLES, A WAX, A HYDROCARBON OIL AND A FATTY ALCOHOL AND/OR A FATTY ACID

CROSS REFERENCE TO RELATED APPLICATIONS

This is a national stage application of PCT/EP2013/062964, filed internationally on Jun. 21, 2013, which claims priority to U.S. Provisional Application Nos. 61/695,321 and 61/695,323, both filed on Aug. 31, 2012, as well as French Application Nos. 1255820 and 1255821, both filed Jun. 21, 2012, all of which are incorporated herein by reference in their entireties.

The present invention relates to a cosmetic composition comprising hydrophobic silica aerogel particles, at least one wax, at least one hydrocarbon oil and at least one fatty alcohol and/or at least one fatty acid, and also to the use of such a composition for hair treatment, especially for the treatment of keratinous fibres and in particular for form retention/shaping of the hair.

Styling products having a wax effect are predominantly provided in the form of more or less viscous pastes which are applied to the hair with the hands.

In point of fact, styling waxes are often tacky and greasy. In addition, the hairstyle obtained is difficult to reposition.

There is therefore a real need to have a cosmetic composition that has good styling and cosmetic properties, and that makes it possible to overcome the drawbacks mentioned above.

The Applicant Company has discovered that, by combining hydrophobic silica aerogel particles, a wax, a hydrocarbon oil and at least one fatty alcohol and/or at least one fatty acid, it is possible to obtain styling waxes with improved qualities of use and improved styling performances.

A subject-matter of the present invention is thus a cosmetic composition comprising:
- hydrophobic silica aerogel particles,
- at least one wax,
- at least one hydrocarbon oil and
- at least one fatty alcohol and/or at least one fatty acid,
- the composition comprising at least 10% by weight of wax(es), with respect to the total weight of the composition.

The cosmetic composition is preferably a composition for styling and/or conditioning keratinous fibres, in particular for styling keratinous fibres, especially human keratinous fibres, such as the hair.

The invention also relates to a method for the cosmetic treatment of keratinous fibres, in particular for form retention and/or shaping of keratinous fibres, employing the cosmetic composition as defined above.

Another subject-matter of the invention is the use of a composition as defined above for hair treatment, in particular for the treatment of keratinous fibres and especially for form retention and/or shaping of the hair.

The composition obtained is easy to distribute in the hands and then over the hair. In addition, the hairstyle is rapid to shape. The hair is not very tacky and a hairstyle having a natural rendering is obtained. The hold of the hairstyle is improved and restyling is facilitated.

Other subject-matters, characteristics, aspects and advantages of the invention will become even more clearly apparent on reading the description and examples which follow.

In that which follows, the expression "at least one" is equivalent to the expression "one or more".

The composition according to the invention comprises hydrophobic silica aerogel particles.

Aerogels are ultralight porous materials which were first produced by Kristler in 1932.

They are generally synthesized by a sol-gel process in a liquid medium and then dried by extraction with a supercritical fluid. The supercritical fluid most commonly used is supercritical $CO_2$. This type of drying makes it possible to avoid shrinkage of the pores and of the material.

Other types of drying also make it possible to obtain porous materials starting from gel, namely (i) drying by freeze drying, which consists in solidifying the gel at low temperature and in then subliming the solvent, and (ii) drying by evaporation. The materials thus obtained are referred to respectively as cryogels and xerogels. The sol-gel process and the various drying operations are described in detail in Brinker C. J. and Scherer G. W., Sol-Gel Science, New York, Academic Press, 1990.

The expression "hydrophobic silica" is understood to mean any silica, the surface of which is treated with silylating agents, for example halogenated silanes such as alkylchlorosilanes, siloxanes, in particular dimethylsiloxanes such as hexamethyldisiloxane, or silazanes, so as to functionalize the OH groups with Si—Rn silyl groups, for example trimethylsilyl groups.

Preferably, the hydrophobic aerogel particles that may be used in the present invention advantageously have a specific surface area per unit of mass (SM) ranging from 500 to 1500 $m^2/g$, preferably from 600 to 1200 $m^2/g$ and better still from 600 to 800 $m^2/g$.

Preferably, the hydrophobic aerogel particles that may be used in the present invention advantageously have an oil absorption capacity, measured at the wet point, ranging from 5 to 18 ml/g of particles, preferably from 6 to 15 ml/g and better still from 8 to 12 ml/g.

Preferably, the hydrophobic aerogel particles that may be used in the present invention advantageously have a size, expressed as the mean diameter (D[0.5]), of less than 1500 μm, preferably ranging from 1 to 30 μm, preferably from 5 to 25 μm, better still from 5 to 20 μm and even better still from 5 to 15 μm.

The hydrophobic aerogel particles used in the present invention may advantageously have a tapped density p ranging from 0.04 $g/cm^3$ to 0.10 $g/cm^3$ and preferably from 0.05 $g/cm^3$ to 0.08 $g/cm^3$.

Preferably, the hydrophobic aerogel particles used in the present invention have a specific surface area per unit of volume SV ranging from 5 to 60 $m^2/cm^3$, preferably from 10 to 50 $m^2/cm^3$ and better still from 15 to 40 $m^2/cm^3$.

According to one preferred embodiment, the hydrophobic aerogel particles according to the invention have a specific surface area per unit of mass (SM) ranging from 500 to 1500 $m^2/g$, preferably from 600 to 1200 $m^2/g$ and better still from 600 to 800 $m^2/g$, a size expressed as the mean diameter (D[0.5]) ranging from 1 to 30 μm and/or an oil absorption capacity measured at the wet point ranging from 5 to 18 ml/g of particles, preferably from 6 to 15 ml/g and better still from 8 to 12 ml/g.

According to another advantageous embodiment, the hydrophobic aerogel particles used in the present invention have a specific surface area per unit of mass (SM) ranging from 600 to 800 $m^2/g$ and a size, expressed as the volume mean diameter (D[0.5]), ranging from 5 to 20 μm and better still from 5 to 15 μm.

The specific surface area per unit of mass can be determined by the nitrogen absorption method, known as the BET (Brunauer-Emmet-Teller) method, described in The Journal of the American Chemical Society, Vol. 60, page 309, February 1938, which corresponds to international standard ISO 5794/1 (appendix D). The BET specific surface area corresponds to the total specific surface area of the particles under consideration.

The absorption capacity measured at the wet point, denoted Wp, corresponds to the amount of oil which needs to be added to 100 g of particles in order to obtain a homogeneous paste.

It is measured according to the "wet point" method or the method for determining the oil uptake of a powder according to the principle described in standard NF T 30-022. It corresponds to the amount of oil adsorbed onto the available surface of the powder and/or absorbed by the powder by measuring the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

The sizes of the aerogel particles according to the invention can be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

In the context of the present invention, this density can be assessed according to the following protocol, known as tapped density protocol:

40 g of powder are poured into a graduated measuring cylinder and then the measuring cylinder is placed on a Stay 2003 device from Stampf Volumeter. The measuring cylinder is subsequently subjected to a series of 2500 tapping actions (this operation is repeated until the difference in volume between two consecutive tests is less than 2%) and then the final volume Vf of tapped powder is measured directly on the measuring cylinder.

The tapped density is determined by the ratio: mass (m)/Vf, in this instance 40/Vf (Vf being expressed in $cm^3$ and m in g).

The specific surface area per unit of volume is given by the relationship:

$$SV=SM*\rho$$

where $\rho$ is the tapped density expressed in $g/cm^3$ and SM is the specific surface area per unit of mass expressed in $m^2/g$, as defined above.

The hydrophobic silica aerogel particles used according to the present invention are preferably silylated silica (INCI name: silica silylate) aerogel particles.

The preparation of hydrophobic silica aerogel particles modified at the surface by silylation is further described in document U.S. Pat. No. 7,470,725.

Use will in particular be made of hydrophobic silica aerogel particles surface-modified with trimethylsilyl groups.

As hydrophobic silica aerogels that may be used in the invention, an example that may be mentioned is the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by Cabot under the references Aerogel TLD 201, Aerogel OGD 201 and Aerogel TLD 203, Enova Aerogel MT 1100 and Enova Aerogel MT 1200.

Use will be made more particularly of the aerogel sold under the name VM-2270 (INCI name: Silica silylate), by the company Dow Corning, the particles of which have a mean size ranging from 5 to 15 microns and a specific surface area per unit of mass ranging from 600 to 800 $m^2/g$.

The hydrophobic silica aerogel particles can be employed in a content ranging from 0.05% to 10% by weight, more preferentially from 0.1% to 5% by weight and more preferentially still from 0.2% to 3% by weight, with respect to the total weight of the composition containing them.

The composition according to the invention also comprises at least one wax.

The waxes under consideration in the context of the present invention are generally deformable or non-deformable solid lipophilic compounds at ambient temperature (25° C.) which exhibit a reversible solid/liquid change in state and which have a melting point of greater than or equal to 30° C. which can range up to 200° C. and in particular up to 120° C.

On bringing one or more waxes in accordance with the invention to the liquid state (melting), it is possible to render it or them miscible with one or more oils and to form a macroscopically homogeneous mixture of wax(es) and oil(s) but, on bringing the temperature of said mixture back to ambient temperature, recrystallization of the wax(es) in the oil(s) of the mixture is obtained.

Within the meaning of the invention, the melting point corresponds to the temperature of the most endothermic peak observed in thermal analysis (DSC) as described in Standard ISO 11357-3; 1999. The melting point of the wax can be measured using a differential scanning calorimeter (DSC), for example the calorimeter sold under the name MDSC 2920 by TA Instruments.

The measurement protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and finally it is subjected to a second temperature rise ranging from −20° C. to 100° C., at a heating rate of 5° C./minute. During the second temperature rise, the variation in the difference in power absorbed by the empty crucible and by the crucible containing the sample of wax is measured as a function of the temperature. The melting point of the compound is the value of the temperature corresponding to the tip of the peak of the curve representing the variation in the difference in power absorbed as a function of the temperature.

The waxes capable of being used in a composition according to the invention are chosen from waxes which are preferably solid at ambient temperature and which are of animal, vegetable, mineral or synthetic origin, and their mixtures. They can be hydrocarbon, esterified, fluorinated and/or silicone waxes.

The wax or waxes capable of being used in the composition according to the invention can be chosen in particular from waxes of mineral origin, such as paraffin wax, ozokerite, ceresin or microcrystalline waxes, such as, for example, the microcrystalline waxes having a melting point of greater than 85° C., such as the products Hi-Mic® 1070, 1080, 1090 and 3080 sold by Nippon Seiro, waxes of vegetable origin, such as carnauba wax, candelilla wax, such as that sold under the reference SP 75 G by Strahl & Pitsch, esparto wax, olive tree wax, rice wax, such as that sold under the reference NC 1720 by Cera Rica Noda, sunflower seed wax, sold by Koster Keunen under the reference sunflower wax, hydrogenated jojoba wax or absolute flower waxes, such as blackcurrant blossom essential wax, or waxes of animal origin, such as beeswaxes or modified beeswaxes (cerabellina); other waxes or waxy starting materials which can be used according to the invention are in particular marine waxes, polyethylene waxes or polyolefin waxes in general, such as α-olefin oligomers, for example the polymers Performa V® 825, 103 and 260 sold by New Phase Technologies, ethylene/propylene copolymers, such as Performalene® EP 700, or Fischer-Tropsch waxes.

Mention may also be made of silicone waxes, such as alkyl or alkoxy dimethicones having from 16 to 45 carbon atoms, or fluorinated waxes.

According to a specific embodiment, the wax used in a composition in accordance with the invention exhibits a melting point of greater than 35° C., better still of greater than 40° C., indeed even of greater than 45° C. or also of greater than 55° C.

Preferably, the wax(es) is(are) chosen from vegetable waxes and mineral waxes.

More preferably, the wax(es) is(are) chosen from mineral waxes.

According to a specific embodiment of the invention, the composition comprises a microcrystalline wax and/or ozokerite.

The composition comprises at least 10% by weight of wax, with respect to the total weight of the composition. The wax content preferentially varies from 10% to 40% by weight, preferably from 10% to 30% by weight and better still from 10% to 20% by weight, with respect to the total weight of the composition.

The composition according to the invention also comprises at least one hydrocarbon oil.

The term "hydrocarbon oil" is understood to mean a hydrocarbon which is composed solely of carbon and hydrogen atoms and which is liquid at normal temperature (25° C.) and at atmospheric pressure (760 mmHg; i.e. $1.013 \times 10^5$ Pa).

More particularly, the hydrocarbon oil according to the invention is chosen from:
  linear or branched, optionally cyclic, lower $C_6$-$C_{16}$ alkanes. Mention may be made, by way of example, of hexane, undecane, dodecane, tridecane or isoparaffins, such as isohexadecane, isododecane and isodecane. Mention may more particularly be made of the mixture of n-undecane ($C_{11}$) and n-tridecane ($C_{13}$),
  linear or branched hydrocarbons of mineral, animal or synthetic origin comprising more than 16 carbon atoms, such as liquid paraffins, liquid petrolatum, polydecenes, hydrogenated polyisobutenes, such as Parleam®, or squalane,
  and their mixtures.

Preferably, the hydrocarbon oil according to the invention is chosen from liquid paraffins, liquid petrolatum, linear lower $C_6$-$C_{16}$ alkanes, such as hexane, undecane, dodecane and tridecane, and their mixtures.

More preferably still, the hydrocarbon oil according to the invention is liquid petrolatum.

The content of hydrocarbon oil(s) preferentially varies from 0.1% to 20% by weight, preferably from 1% to 15% by weight and better still from 1% to 5% by weight, with respect to the total weight of the composition.

The composition according to the invention can also comprise at least one fatty alcohol.

The fatty alcohol can be liquid or non-liquid.

The term "liquid fatty alcohol" is understood to mean a non-glycerolated and non-oxyalkylenated fatty alcohol which is liquid at normal temperature (25° C.) and at atmospheric pressure (760 mmHg, i.e. $1.013 \times 10^5$ Pa).

Preferably, the liquid fatty alcohols of the invention comprise from 8 to 30 carbon atoms.

The liquid fatty alcohols of the invention can be saturated or unsaturated.

The saturated liquid fatty alcohols are preferably branched. They can optionally comprise, in their structure, at least one aromatic or non-aromatic ring. They are preferably acyclic.

More particularly, the saturated liquid fatty alcohols of the invention are chosen from octyldodecanol, isostearyl alcohol and 2-hexyldecanol.

Octyldodecanol is very particularly preferred.

The unsaturated liquid fatty alcohols exhibit, in their structure, at least one double or triple bond and preferably one or more double bonds. When several double bonds are present, there are preferably 2 or 3 of them and they can be conjugated or unconjugated.

These unsaturated fatty alcohols can be linear or branched.

They can optionally comprise, in their structure, at least one aromatic or non-aromatic ring. They are preferably acyclic.

More particularly, the unsaturated liquid fatty alcohols of the invention are chosen from oleyl alcohol, linoleyl alcohol, linolenyl alcohol and undecylenyl alcohol.

Oleyl alcohol is very particularly preferred.

The non-liquid fatty alcohols suitable for the implementation of the invention are chosen more particularly from saturated or unsaturated and linear or branched alcohols comprising from 8 to 30 carbon atoms. Mention may be made, for example, of cetyl alcohol, stearyl alcohol and their mixtures (cetearyl alcohol).

Preferably, the fatty alcohol is non-liquid and is preferably solid.

Preferably, the fatty alcohol is chosen from cetyl alcohol, stearyl alcohol and their mixtures.

Preferably, the composition comprises at least one fatty alcohol.

When it comprises it (them), the fatty alcohol(s) is (are) present in the composition in a content ranging from 0.1% to 20% by weight, preferably from 0.5% to 10% by weight and better still from 1% to 5% by weight, with respect to the total weight of the composition.

The composition according to the invention can also comprise at least one fatty acid.

The fatty acid can be liquid or non-liquid.

The term "liquid fatty acid" is understood to mean a fatty acid which is liquid at normal temperature (25° C.) and at atmospheric pressure (760 mmHg, i.e. $1.013 \times 10^5$ Pa).

Preferably, the liquid fatty acids of the invention comprise from 8 to 30 carbon atoms.

The liquid fatty acids of the invention can be saturated or unsaturated.

The saturated liquid fatty acids are preferably branched. They can optionally comprise, in their structure, at least one aromatic or non-aromatic ring. They are preferably acyclic.

Mention may more particularly be made of isostearic acid.

The unsaturated liquid fatty acids exhibit, in their structure, at least one double or triple bond and preferably one or more double bonds. When several double bonds are present, there are preferably 2 or 3 of them and they can be conjugated or unconjugated.

These unsaturated fatty acids can be linear or branched.

They can optionally comprise, in their structure, at least one aromatic or non-aromatic ring. They are preferably acyclic.

Mention may be made, as unsaturated fatty acid, of oleic acid.

Preferably, the fatty acid is non-liquid and is preferably solid.

The non-liquid fatty acids suitable for the implementation of the invention are chosen more particularly from saturated or unsaturated and linear or branched acids comprising from 8 to 30 carbon atoms.

Mention will be made, for example, as fatty acid, of stearic acid, palmitic acid, myristic acid, behenic acid and their mixtures.

Preferably, the composition comprises at least one fatty acid.

The fatty acid(s) can be present in the composition in a content ranging from 0.1% to 20% by weight, preferably from 0.5% to 10% by weight and better still from 1% to 5% by weight, with respect to the total weight of the composition.

The cosmetic composition according to the invention can optionally comprise one or more surfactants which can be chosen from anionic, cationic, non-ionic, amphoteric or zwitterionic surfactants and their mixtures.

Preferably, the surfactant(s) is (are) chosen from non-ionic surfactants.

The non-ionic surfactants which can be used in the compositions of the present invention are compounds well known per se (see in particular in this respect "Handbook of Surfactants" by M. R. Porter, published by Blackie & Son (Glasgow and London), 1991, pp. 116-178). They are chosen in particular from polyethoxylated, polypropoxylated or polyglycerolated fatty alcohols, polyethoxylated, polypropoxylated or polyglycerolated α-diols or polyethoxylated, polypropoxylated or polyglycerolated ($C_{1-20}$)alkylphenols, the fatty chain comprising, for example, from 8 to 18 carbon atoms, it being possible for the number of ethylene oxide or propylene oxide groups to range in particular from 1 to 150 and for the number of glycerol groups to range in particular from 1 to 30.

Mention may also be made of condensates of ethylene oxide and of propylene oxide with fatty alcohols, polyethoxylated fatty amides preferably having from 1 to 100 ethylene oxide units, polyglycerolated fatty amides comprising on average from 1 to 5 and in particular from 1.5 to 4 glycerol groups, ethoxylated fatty acid esters of sorbitan having from 1 to 50 ethylene oxide units, fatty acid esters of sucrose, fatty acid esters of polyethylene glycol, alkyl polyglycosides, polyethoxylated vegetable oils preferably having from 1 to 100 ethylene oxide units, N—($C_{6-24}$ alkyl)glucamine derivatives or amine oxides, such as ($C_{10-14}$ alkyl)amine oxides or N—($C_{10-14}$ acyl)aminopropylmorpholine oxides.

The alkyl polyglucosides can be chosen, for example, from decyl glucoside (($C_9/C_{11}$ alkyl) (1,4)polyglucoside), such as the product sold under the name Mydol 10® by Kao Chemicals or the product sold under the name Plantacare 2000 UP® by Henkel and the product sold under the name Oramix NS 10® by SEPPIC; caprylyl/capryl glucoside, such as the product sold under the name Plantacare KE 3711® by Cognis or Oramix CG 110® by SEPPIC; lauryl glucoside, such as the product sold under the name Plantacare 1200 UP® by Henkel or Plantaren 1200 N® by Henkel; coco glucoside, such as the product sold under the name Plantacare 818 UP® by Henkel; caprylyl glucoside, such as the product sold under the name Plantacare 810 UP® by Cognis; and their mixtures.

When it comprises it (them), the surfactant(s) is (are) present in a content ranging from 0.01% to 20% by weight, preferably in a content ranging from 0.1% to 15% by weight, with respect to the total weight of the composition.

The composition according to the invention can also comprise one or more thickening agents which can be chosen from polymeric thickeners, which are natural or synthetic and associative or non-associative, and non-polymeric thickeners.

Mention may be made, as polymeric thickening agents, for example, of cellulose thickening agents, for example hydroxyethylcellulose, hydroxypropylcellulose and carboxymethylcellulose, guar gum and its derivatives, for example hydroxypropyl guar, sold by Rhodia under the reference Jaguar HP 105, gums of microbial origin, such as xanthan gum and scleroglucan gum, carrageenan, for example the carrageenan powder sold by Cargill under the reference Satiagum UTC 30, synthetic polymeric thickening agents resulting from radical polymerization reactions or polycondensation reactions, such as crosslinked homopolymers of acrylic acid or of acrylamidopropanesulfonic acid, for example the Carbomer products, or non-ionic, anionic or amphoteric associative polymers, such as the polymers sold under the names Pemulen TR1 or TR2 by Goodrich, Salcare SC90 by Allied Colloids, Aculyn 22, 28, 33, 44 or 46 by Rohm & Haas and Elfacos T210 and T212 by Akzo, or else sodium polyacrylate, such as the product sold by Sensient under the commercial reference Covacryl MV 60.

When it comprises it (them), the thickening agent(s), preferably polymeric thickening agent(s), is (are) present in a content ranging from 0.1% to 10% by weight, preferably in a content ranging from 0.2% to 5% by weight, with respect to the total weight of the composition.

Preferably, the composition comprises water, preferably at a content of greater than or equal to 5% by weight, with respect to the total weight of the composition. The water content preferentially varies from 5% to 98% by weight, preferably from 10% to 95% by weight, better still from 20% to 80% by weight and even better still from 30% to 70% by weight, with respect to the total weight of the composition.

The composition can also comprise one or more water-soluble liquid organic solvents preferably chosen from monoalcohols, such as ethanol or isopropanol; polyols, such as propylene glycol, butylene glycol or glycerol; polyol ethers; and their mixtures.

The composition according to the invention can comprise a propellant. Mention may be made, for example, of liquefied gases, such as dimethyl ether, 1,1-difluoroethane or $C_{3-5}$ alkanes, for instance propane, isopropane, n-butane, isobutane or pentane, or compressed gases, such as air, nitrogen or carbon dioxide, and their mixtures.

Mention may preferentially be made of $C_{3-5}$ alkanes and in particular propane, n-butane and isobutane, and their mixtures.

When it comprises it (them), the composition comprises one or more propellant(s) in an amount ranging from 1% to 60% by weight, better still from 2% to 50% by weight and more preferentially still from 4% to 40% by weight, with respect to the total weight of the composition.

The composition for form retention and/or shaping of the hair according to the invention can additionally comprise one or more additives, other than the compounds of the invention, chosen from fixative polymers, non-silicone conditioning agents, silicones, vitamins and provitamins, including panthenol, sunscreens, pearlescent agents and opacifying agents, dyes, sequestering agents, plasticizing agents, solubilizing agents, acidifying agents, basifying agents, neutralizing agents, antioxidants, antifoaming agents, moisturizing agents, emollients, hydroxy acids, penetrating agents, fragrances, preservatives and fillers and particles of solid type other than the aerogels, such as, for example, coloured or colourless and inorganic or organic pigments.

These additives can be present in the composition according to the invention in an amount ranging from 0% to 20% by weight, with respect to the total weight of the composition.

Of course, a person skilled in the art will take care to choose the optional additional compounds and/or their amounts in such a way that the advantageous properties of the compositions used according to the invention are not, or not substantially, detrimentally affected by the envisaged addition.

According to a specific embodiment, the cosmetic composition comprises hydrophobic silica aerogel particles, at least one mineral wax, at least one hydrocarbon oil and at least one fatty alcohol and/or one fatty acid, the composition comprising at least 10% by weight of mineral wax(es), with respect to the total weight of the composition.

The composition according to the invention can be provided inter alia in the form of liquids which are thickened to a greater or lesser degree, gels, serums, creams, pastes, sprays or mousses.

In particular, the composition of the invention can be applied using an aerosol device.

Preferably, the composition according to the invention is provided in the form of gels, creams or pastes.

The cosmetic composition according to the invention can advantageously be used for the cosmetic treatment of the hair. In particular, the composition can be employed for styling the hair, for example for shaping and/or form retention of the hairstyle.

The present invention also relates to a method for the cosmetic treatment of the hair, for example a method for shaping and/or form retention of the hairstyle, which consists in applying, to the hair, an effective amount of a composition according to the invention as described above and in then carrying out an optional rinsing after an optional leave-in time.

Preferably, the composition according to the invention is not rinsed off.

The method of the invention can be carried out at ambient temperature (25° C.) or under heat at a temperature varying from 40° C. to 230° C. using any heating device: hood, hairdryer or iron.

The invention is illustrated in more detail in the following example, which is presented by way of illustration and without implied limitation of the invention.

EXAMPLE

A styling paste was prepared from the ingredients shown as percentage by weight of product as is in the table below:

| Chemical name | % |
| --- | --- |
| Fragrance | 0.6 |
| 1,3-Butylene glycol | 3 |
| Liquid petrolatum[1] | 2 |
| Mineral wax formed of hydrocarbons ($C_{20}/C_{60}$)[2] | 11 |
| Sorbitol as a 70% aqueous solution | 3 |
| Trimethylated silica[3] | 1 |
| Oxyethylenated stearyl alcohol (2 EO)[4] | 4 |
| Glyceryl caprylate | 0.5 |
| Triethanolamine (99%) | 1.2 |
| Myristyl/cetyl/stearyl myristate/palmitate/stearate mixture[5] | 7 |
| Disodium ethylenediaminetetraacetate dihydrate | 0.1 |
| 1,2-Octanediol | 0.5 |
| 2-Phenoxyethanol | 0.9 |
| Fatty acids of vegetable origin (stearic acid at 53% - palmitic acid-myristic acid)[6] | 3 |
| Polydimethylsiloxane (viscosity 5 cSt) | 7.5 |
| Microcrystalline wax (melting point 74-79° C.)[7] | 7 |
| Carboxyvinyl polymer[8] | 0.2 |
| Oxyethylenated oleocetyl alcohol (30 EO)[9] | 6 |
| Water | q.s. for 100 |

[1] Blandol, sold by Sonneborn
[2] Ozokerite Wax SP 1020 P, sold by Strahl & Pitsch
[3] VM-2270 Aerogel Fine Particles, sold by Dow Corning
[4] Brij S2-SO-(SG), sold by Croda
[5] Crodamol MS-PA-(MH), sold by Croda
[6] Palmera B1802CG, sold by KLK Oleo
[7] White Microcrystalline Wax SP-18, sold by Strahl & Pitsch
[8] Synthalen K, sold by 3V
[9] Eumulgin O 30, sold by Cognis This cream was applied to dry hair.

The cream obtained is easy to withdraw and to spread in the hands. It can be easily transferred from the hands to the hair and it is easy to distribute over the hair. The cream is not very tacky but sufficiently so to shape the hairstyle. In addition, the hairstyle is rapid to shape.

A hairstyle with a natural rendering is obtained. The hair does not clump together and, in addition, a mat effect is obtained.

Good hold of the hairstyle, which is lasting, and which is in addition easy to restyle, is obtained.

The invention claimed is:

1. A cosmetic composition comprising:
   hydrophobic silica aerogel particles;
   at least one wax;
   at least one hydrocarbon oil; and
   at least one fatty compound chosen from fatty alcohols or fatty acids;
   wherein the composition comprises at least 10% by weight of wax, relative to the total weight of the composition, and
   wherein the hydrophobic silica aerogel particles are present in the composition in an amount ranging from about 0.05% to about 10% by weight, relative to the total weight of the composition,
   wherein the hydrophobic silica aerogel particles exhibit a size, expressed as mean diameter (D[0.51]), ranging from about 1 to about 30 um,
   wherein the hydrophobic aerogel particles exhibit a specific surface per unit of weight (Sw) ranging from about 500 to about 1500 $m^2/g$, and
   wherein the hydrophobic aerogel particles exhibit an oil absorption capacity, measured at the wet point, ranging from about 5 to about 18 ml/g.

2. The composition of claim 1, wherein the hydrophobic silica aerogel particles are particles of hydrophobic silica surface-modified with trimethylsilyl groups.

3. The composition of claim 1, wherein the hydrophobic silica aerogel particles exhibit a packed density p ranging from about 0.04 g/cm$^3$ to about 0.10 g/cm$^3$.

4. The composition of claim 1, wherein the hydrophobic silica aerogel particles exhibit a specific surface per unit of volume Sv ranging from about 5 to about 60 m$^2$/cm$^3$.

5. The composition of claim 1, wherein the hydrophobic silica aerogel particles are present in the composition in an amount ranging from about 0.1% to about 5% by weight, relative to the total weight of the composition.

6. The composition of claim 1, wherein the at least one wax is chosen from vegetable waxes and mineral waxes.

7. The composition of claim 1, wherein the at least one wax is chosen from microcrystalline waxes and ozokerite.

8. The composition of claim 1, wherein wax is present in the composition in an amount ranging from about 10% to about 40% by weight, relative to the total weight of the composition.

9. The composition of claim 1, wherein the at least one hydrocarbon oil is chosen from liquid paraffins, liquid petrolatum, linear lower $C_6$-$C_{16}$ alkanes.

10. The composition of claim 1, wherein hydrocarbon oil is present in the composition an amount ranging from about 0.1% to about 20% by weight, relative to the total weight of the composition.

11. The composition of claim 1, wherein the at least one fatty compound is choden from fatty alcohols, and wherein the at least one fatty alcohol is chosen from cetyl alcohol, stearyl alcohol, behenyl alcohol and mixtures thereof.

12. The composition of claim 1, wherein the at least one fatty compound is choden from fatty alcohols, and wherein the at least one fatty acid chosen from stearic acid, palm acid, myristic acid, behenic acid and mixtures thereof.

13. The composition of claim 1, wherein the at least one fatty compound is choden from fatty alcohols, and wherein the fatty acid(s) is present in the composition in an amount ranging from about 0.1% to 20% by weight, relative to the total weight of the composition.

14. The composition of claim 1, wherein the at least one fatty compound is choden from fatty alcohols, and wherein the fatty alcohol(s) is present in the composition in an amount ranging from of about 0.1% to 20% by weight, relative to the total weight of the composition.

15. The composition of claim 1, comprising water in an amount ranging from about 5% to about 98% by weight, relative to the total weight of the composition.

16. A method for the cosmetic treatment of keratinous fibers comprising: applying to the keratinous fibers an effective amount of a composition comprising:
hydrophobic silica aerogel particles;
at least one wax;
at least one hydrocarbon oil; and
at least one fatty compound chosen from fatty alcohols or fatty acids;
wherein the composition comprises at least 10% by weight of wax, relative to the total weight of the composition,
wherein the hydrophobic silica aerogel particles are present in the composition in an amount ranging from about 0.05% to about 10% by weight, relative to the total weight of the composition,
wherein the hydrophobic silica aerogel particles exhibit a size, expressed as mean diameter (D[0.51]), ranging from about 1 to about 30 um,
wherein the hydrophobic aerogel particles exhibit a specific surface per unit of weight (Sw) ranging from about 500 to about 1500 m$^2$/g, and
wherein the hydrophobic aerogel particles exhibit an oil absorption capacity, measured at the wet point, ranging from about 5 to about 18 ml/g.

17. A method for shaping the hair comprising: applying to the hair an effective amount of a composition comprising:
hydrophobic silica aerogel particles;
at least one wax;
at least one hydrocarbon oil; and
at least one fatty compound chosen from fatty alcohols or fatty acids;
wherein the composition comprises at least 10% by weight of wax, relative to the total weight of the composition,
wherein the hydrophobic silica aerogel particles are present in the composition in an amount ranging from about 0.05% to about 10% by weight, relative to the total weight of the composition,
wherein the hydrophobic silica aerogel particles exhibit a size, expressed as mean diameter (D[0.51]), ranging from about 1 to about 30 um,
wherein the hydrophobic aerogel particles exhibit a specific surface per unit of weight (Sw) ranging from about 500 to about 1500 m$^2$/g, and
wherein the hydrophobic aerogel particles exhibit an oil absorption capacity, measured at the wet point, ranging from about 5 to about 18 ml/g.

* * * * *

UNITED STATES PATENT AND TRADEMARK OFFICE
CERTIFICATE OF CORRECTION

PATENT NO. : 10,588,850 B2
APPLICATION NO. : 14/410265
DATED : March 17, 2020
INVENTOR(S) : Thomas Fondin et al.

Page 1 of 1

It is certified that error appears in the above-identified patent and that said Letters Patent is hereby corrected as shown below:

On the Title Page

Should read 19 Claims, No Drawings.

In the Claims

Claim 11, Column 11, Line 29, change "choden" to -- chosen --.

Claim 12, Column 11, Line 34, change "choden" to -- chosen --; and

Claim 12, Column 11, Line 35, change "palm" to -- palmitic --.

Claim 13, Column 11, Line 38, change "choden" to -- chosen -- and change "alcohols" to -- acids --.

Claim 14, Column 11, Line 43, change "choden" to -- chosen --.

Claim 16, Column 12, Line 17, change "(D[0.51])" to -- (D[0.5]) --.

Claim 17, Column 12, Line 40, change "(D[0.51])" to -- (D[0.5]) --.

Signed and Sealed this
Nineteenth Day of May, 2020

Andrei Iancu
*Director of the United States Patent and Trademark Office*